United States Patent
Alvarado et al.

(10) Patent No.: US 9,427,484 B1
(45) Date of Patent: Aug. 30, 2016

(54) CLOTH AND FABRIC STERILIZER UTILIZING UPRIGHT HOLDING TUB

(71) Applicants: Jose Alvarado, Fairfield, CT (US); Jean Zamora, Fairfield, CT (US)

(72) Inventors: Jose Alvarado, Fairfield, CT (US); Jean Zamora, Fairfield, CT (US)

(*) Notice: Subject to any disclaimer, the term of this patent is extended or adjusted under 35 U.S.C. 154(b) by 10 days.

(21) Appl. No.: 14/121,926

(22) Filed: Nov. 4, 2014

(51) Int. Cl.
| | |
|---|---|
| A47K 7/00 | (2006.01) |
| A61L 2/07 | (2006.01) |
| D06B 5/22 | (2006.01) |
| D06B 5/24 | (2006.01) |
| D06B 23/04 | (2006.01) |
| D06B 23/18 | (2006.01) |

(52) U.S. Cl.
CPC . *A61L 2/07* (2013.01); *D06B 5/22* (2013.01); *D06B 5/24* (2013.01); *D06B 23/04* (2013.01); *D06B 23/18* (2013.01); *D10B 2509/026* (2013.01)

(58) Field of Classification Search
CPC ........................................ A61L 2/07
See application file for complete search history.

(56) References Cited

U.S. PATENT DOCUMENTS 3,902,044 A * 8/1975 Doyle .................... A47G 21/16
126/369

* cited by examiner

*Primary Examiner* — Michael Barr
*Assistant Examiner* — Jason Riggleman
(74) *Attorney, Agent, or Firm* — H. Gibner Lehmann

(57) ABSTRACT

A household sterilizer for disinfecting fabric material that has become soiled. The unit involves an upright tub containing an electric heating element at its base. A suspension bar extends generally across at least part of the tub interior, for hanging clothing to be treated. An electric cord for the heating element has a switch and timer module in series, to control current flow to the heating element. The arrangement is such that a wide variety of garments, including miscellaneous fabrics in general, can be readily steam cleaned with a minimum of water being required. The tub occupies a minimum of space, suitable for a conventional home or apartment.

7 Claims, 5 Drawing Sheets

CLOTH AND FABRIC STERILIZER UTILIZING UPRIGHT HOLDING TUB

NO CROSS REFERENCE TO RELATED APPLICATIONS

Field of the Invention

The present invention relates generally to systems for cleaning clothing and/or fabric material of the type typically warn by both children and adults, including miscellaneous fabrics, undergarments and canvas/composition footwear.

Background of the Invention

There exist an extremely large number of patents involving methods and devices for accomplishing the task of cleaning articles of all types, from miscellaneous fabrics to dress garments and undergarments, to canvas shoes, and even formal draperies. For clothing, the general objective is to eliminate incidental oils and waste substances as for example, those of a type routinely secreted from the wearer's body. This includes cell bacteria, cell viruses, and less dangerous substances in the form of stains of all types. Also, even lightly soiled clothing often presents a generally disheveled appearance, such as wrinkling, bunching of the fabric, and creasing and/or shrinkage.

In addition to water-based cleaning solutions, much existing industrial machinery has been developed, using carbon dioxide gas (under high pressure), and perfluorobutylamine, a cleaning fluid that is mostly insoluble in water. Such substances, while capable of removing certain oily residues, are incapable of dissolving some water-based contaminants commonly found on undergarments, and on sportswear for warm weather, as when athletic shorts, T-shirts, Spandex, and the like are typically worn.

Unfortunately, for a particular garment, the useful life deteriorates with each subsequent cleaning, which is often dependent of the particular method used.

Most cleaning in use today is undertaken by a dry-cleaner who operates out of a store front and does business with walk-in consumers. Much of the actual processing is carried out at a location remote from the store front, and thus there is a delay in the frequency with which a garment can be worn due to the turnaround time spent with the drycleaner.

Home-based cleaning equipment as utilized in American households consists of washer-dryer combinations, and the washing step relies on a water-soluble soap or detergent. Also noteworthy is that such households almost never have direct access to the larger equipment of the type utilized by the dry cleaning industry.

An exhaustive listing of cleaning methods and apparati is apparent from the prior art citations made in U.S. Pat. No. 6,898,951, issued to J. C. Severns et al, and assigned to Proctor and Gamble Corp., Cincinnati, Ohio. Since a detailed inspection of all of this art would take many days, reliance on the specific disclosures thereof cannot be readily established. Nor is the list being claimed as having been considered in this single Utility patent application, as presented here.

Thus, there is still improvement needed in the field of simplified household-based treatments and sterilization techniques, as well as appliances for use in the home.

Particularly, techniques for reducing the amount of water required by a typical household washing machine, have progressed only moderately in the recent past.

SUMMARY OF THE INVENTION

Accordingly an object of the present invention is to provide an improved household apparatus that is straightforward in its construction, and simple to install and use.

A related object is to provide an improved apparatus as above set forth, which utilizes a minimum of water, thereby saving in the expense thereof, and largely eliminating resultant tub loads of waste water from being exhausted to sewer lines, and thereafter to water purification plants.

Still another object is to provide an improved apparatus of the kind indicated, which is physically small enough to comfortably fit into a typical laundry room of the type used in today's home or apartment facility.

Yet another object is to provide an improved apparatus as above characterized, which effectively sterilizes and disinfects a variety of products, from outer garments, cloth diapers, underwear, and footwear, to other miscellaneous fabrics desired to be treated.

The invention provides a household sterilizer apparatus for decontaminating soiled cloth material such as diapers or clothing, comprising in combination an upright tub having an open top terminating in a lip, a bottom wall constituting a base, and a vertical side wall, a closure member adapted to fit over said tub lip, an electrical heater disposed at the base of the tub, said heater having a heat insulating outer housing, and an upper surface providing a hot plate, a removable metal pan having a diametric handle, said pan having a bottom wall adapted to be seated on said hot plate, a quantity of water in said pan, to be vaporized into steam and water vapor, said steam and water vapor filling the tub interior and coming into contact with the diapers or clothing so as to clean the same, a suspension structure consisting of a cross bar extending from one side of the tub interior to an opposite side thereof, for suspending said cloth material in the tub downward of the tub lip and in the path of the generated steam emanating from the metal pan, and an electrically powered venting fan disposed in the side wall of said tub, for introducing air from outside the tub into the tub interior, and displacing residual steam and water vapor therein, and an electrical control for either operating the venting fan or for interrupting power from the fan, accessible from outside of the tub.

Other features and advantages will hereinafter appear.

BRIEF DESCRIPTION OF THE DRAWINGS

In the drawings, illustrating preferred embodiments of the invention.

DESCRIPTION OF THE PREFERRED EMBODIMENTS, AND BEST MODES CONTEMPLATED FOR CARRYING OUT THE INVENTION, AS OF THE PRESENT DATE

Figure 1:
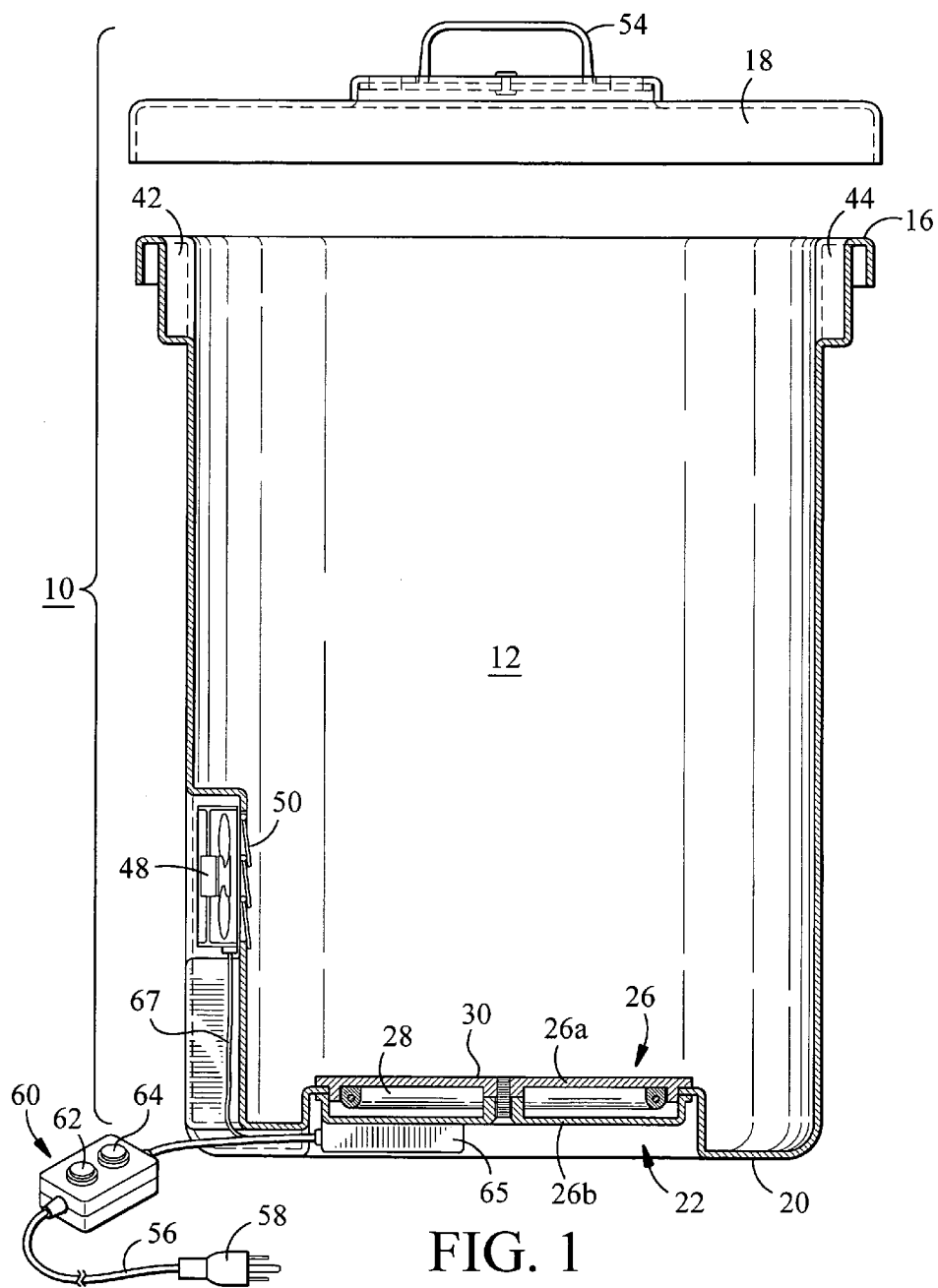
FIG. 1 is an axial sectional view of portions of the improved fabric sterilizer of the present invention, but with the supporting structures for the fabric removed, for clarity.

Referring first to FIG. 1, there is illustrated the improved household sterilizer device of the present invention. The unit is intended for consumer use, and is especially adapted for steam/hot water vapor disinfecting of cloth/fabric material, such as baby diapers, lightweight towels, and/or clothing in the nature of fabric slippers or sneakers.

The household sterilizer device is generally designated by the numeral 10, comprising an upright tub 12 of generally cylindrical configuration, having an open top 14 that is bounded by an outturned lip 16. The tub lip 16 is fitted with a circular lid designated 18. The tub bottom wall 20 constitutes a base, which is provided with central downwardly-facing recess 22. The bottom wall exterior to the recess is intended to be placed on a floor or other convenient surface in the household.

Optionally, the lip 16 or lid 18 may be fitted with a resilient peripheral gasket (not shown) of suitable rubber or plastic substance, resistant to softening under conditions of heat.

Further, by the invention there is provided, secured to the inside of the bottom wall, an insulated housing 26 containing a heating element 28. The housing has two parts, an upper part 26a and a lower part 26b, and the two parts fit together to confine the heating element 28. The upper part of the housing has a substantially flat surface constituting a hot-plate. The housing 26 is constituted of heat-resistant material, such as ceramic, or silicon in the form of a sand and adhesive mixture, or heat-resistant glass. The heating element 28, can be constituted as a simple tungsten-containing compound, or other known material similar to what has come to be known in the field as a Calrod. Further, where the housing parts 26a, 26b join, there is formed an annular groove which accepts an inwardly extending flange on the inner surface of the recess 22 of the tub bottom wall 20, such that the housing 26 and its heating element 28 are held captive in position on the underside of the tub, as in FIGS. 1-4 and 5. A metal pan or container 36 is provided, constituting a water reservoir to rest on the hot-plate. The pan has a depending annular flange 38 which telescopes over the wall of the tub recess 22, and is centralized thereby. Preferably the pan 36 has a curved diametric handle 40, FIGS. 4 and 5, by which it can be manually removed when cool, so as to enable it to be periodically stripped of mineral deposits that inevitably form following continued refill and evaporation cycles, as will be explained further in the description which follows.

There is further provided, near the upper part of the tub, an inwardly, diametrically opposed notch pair 42, 44. This in turn provides a seat for a suspension rod or hanger 46, FIGS. 2 and 5, which preferably can be a rigid plastic tube or a metal pipe constituted from plastic, stainless steel or other suitable non-corrosive material. The rod or hanger 46 can be easily installed or removed when the lid 18 of the tub 12 is removed, as can be readily understood from FIGS. 1 and 5.

In addition, the invention provides, in the tub side wall, an electric fan 48, preferably a muffin fan, which can be electrically energized by a control system to be described. As illustrated in FIG. 1-4, the fan 48 is mounted in a recess in the tub side wall, and is arranged to suck air from the room exterior, into the interior of the tub, for drying out the contents, following their heated disinfecting process. In order to effect isolation between the tub exterior and interior when the fan 48 is dormant, shutters 50 are provided, in the form of horizontal slats arranged to pivot inwardly under the action of the muffin fan 48 when it is operating. The shutters 50 open when the fan is energized, and close under the action of gravity when the fan is inoperative.

Also, by the invention, the lid 18 of the tub contains a manually operated shutter 52 which may be conveniently operated by a handle 54 for the lid. Turning of the handle 54 results in opening/or closing of the lid shutter 52, as desired. Either the "powered" venting provided by the fan 48 or the "passive" venting enabled at the tub lid shutter 52 can be used when it is desired to draw room air into the tub interior, or exhaust vapor from the tub interior, as can be readily understood.

In FIG. 1, the heating element 28 is powered through a conventional electric cord 56 having the usual three prong, 110 volt grounding-style plug 58 attached. The muffin fan 48 is also powered through this cord via an electric lead designated 67. Item 65 is merely a junction box, providing proper connections between the respective switch 62, 64 through the cord 56, and the heating element 28 or the muffin fan 48.

As shown in FIG. 1, there is inserted in series with the cord 56, a combination timer and electric switch module 60, for selectively controlling separately and independently, the operation of the heating element 28 and muffin fan 48. In particular, the combination timer and switch module 60 provides for two individual push-button switches 62, 64 respectively, that are both accessible to the user. One push button switch 62 controls the heating element and the other 64 operates the fan 48. As an example, the circuitry (not shown) is arranged so that depression of the one button 62 begins a timed, 3-20 minute interval (or longer, if desired) of power supplied to the heating element 28, such power being interrupted automatically at the end of the said interval.

The module 60 is preferably made using components standard in the electronic art. Since these components are known per se, for timing functions, further discussion and detailed illustration of the specific arrangement is omitted, in the interest of simplicity.

Overload protection, or provision against overheating of the heating element is also preferably included in such module 60. This feature, though not shown, is also considered to be implicit in the existing electronic field.

Figure 2:
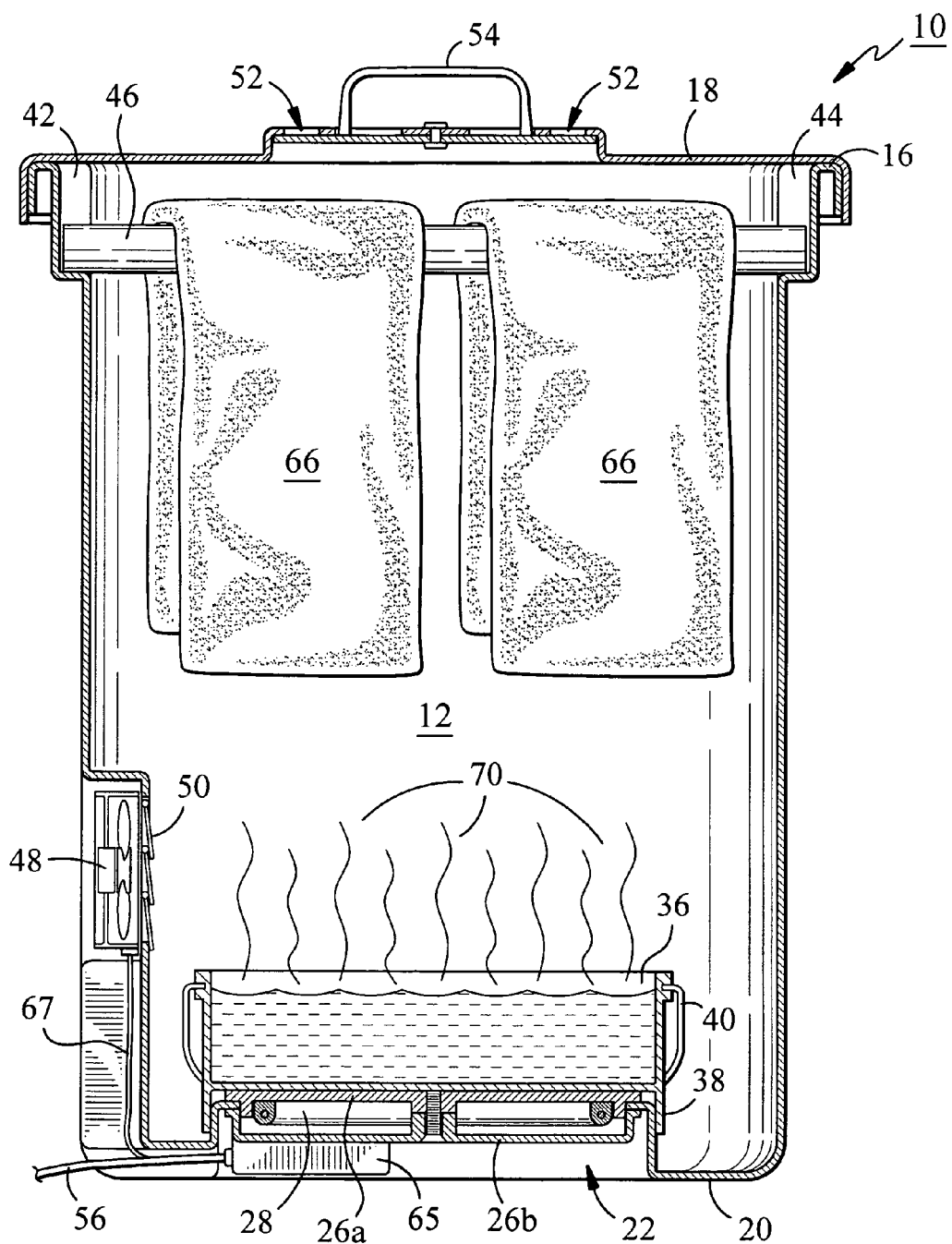
FIG. 2 is a view like FIG. 1, with two cloth/fabric items suspended in the sterilizer, ready to be cleaned.
Figure 3:
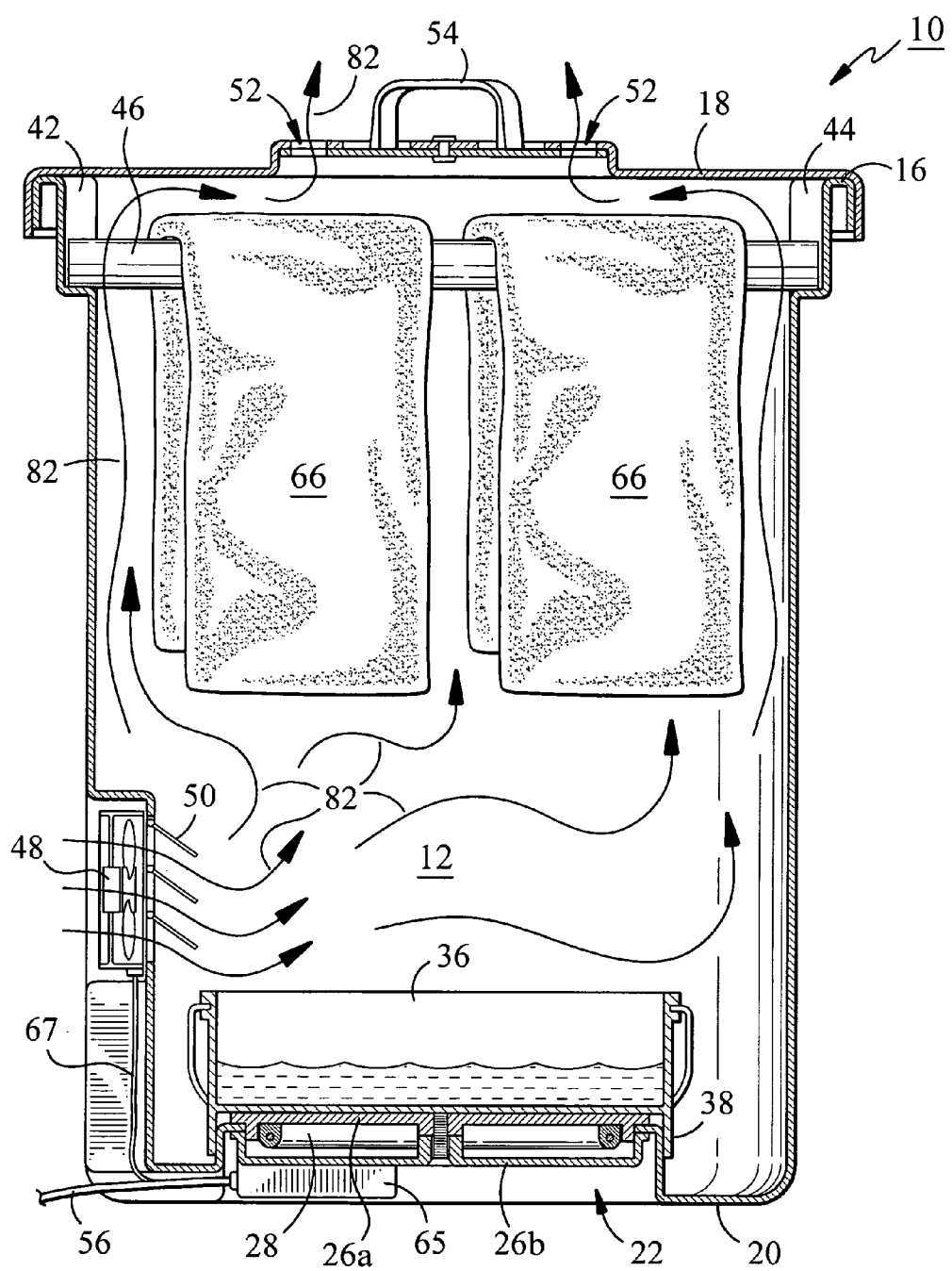
FIG. 3 is a view like FIG. 2 showing the nature of air flow when a powered vent in the side wall of the sterilizer is operated.
Figure 6:
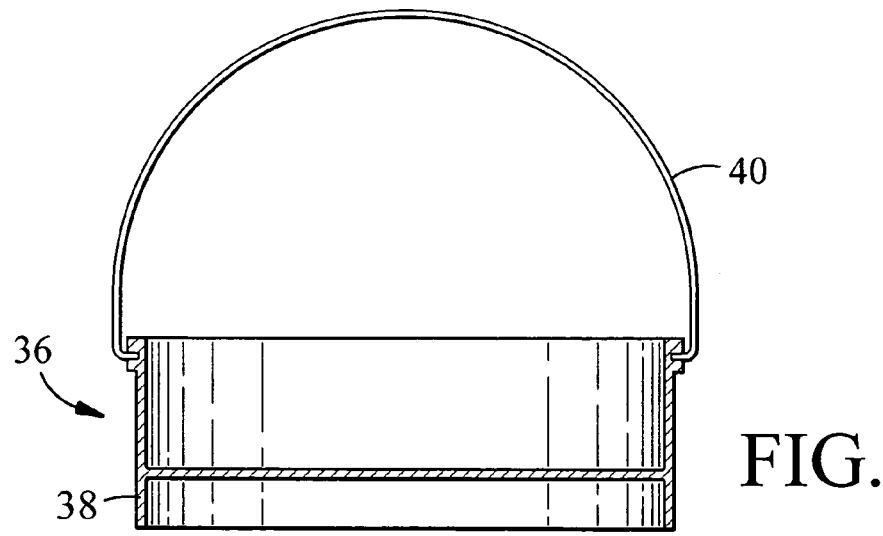
FIG. 6 is a view, partly in axial section and partly in front elevation, of a pan or container as utilized in the sterilizer, for containing tap water to be vaporized into steam/water vapor in readiness for cleaning to commence.

In FIGS. 2 and 3, when it is desired to use the sterilizer for clothing designated 66, the latter can be suspended from the bar 46 as shown, hanging pendant therefrom, disposed above the pan 36. A predetermined quantity of water is first poured into the pan when it is outside of the tub, and thereafter the pan installed in position onto the hot-plate. The pan is provided with a curved diametric wire handle 40, FIG. 6, to facilitate grasping it, and manipulating it into and out of the tub.

Subsequent to filling the pan, the lid 18 is closed. The push button switch 62 for the heating element 28 is then depressed, thus energizing the heating element and heating the water in the pan for the predetermined timed interval mentioned hereinabove. This in turn generates a cloud of steam/heated water vapor 70, FIG. 2, which travels upward through the suspended clothing 66, and permeates the fabrics thereof. In operation, it is preferred that the temperature be sufficient to destroy most bacteria and virus forms of the type that commonly accumulate in clothing, following wearing thereof. Thus, the clothing 66 being treated is steamed for such predetermined time interval. A heating cycle is thereby produced, and expiration of the cycle is designed to roughly coincide with the time it takes for a desired amount of steam to be generated, and for the water in the pan 36 to be depleted. The timing cycle, once completed, re-sets itself until the next actuation of the switch 62. The tub lid 18 may then be slowly opened using care not to burn oneself, and the disinfected clothing can be removed; alternatively, the clothing can be subjected to a drying period while still in place in the tub, by energization of the switch 64, to allow some of the residual moisture to evaporate. With operation of the fan 48, air will be drawn from the room, past the (open) shutters and flow in accordance with the arrows 82 shown in FIG. 3. For full circulation, the passive vent 52 in the lid 18 should also be open, as can be readily understood.

Figure 4:
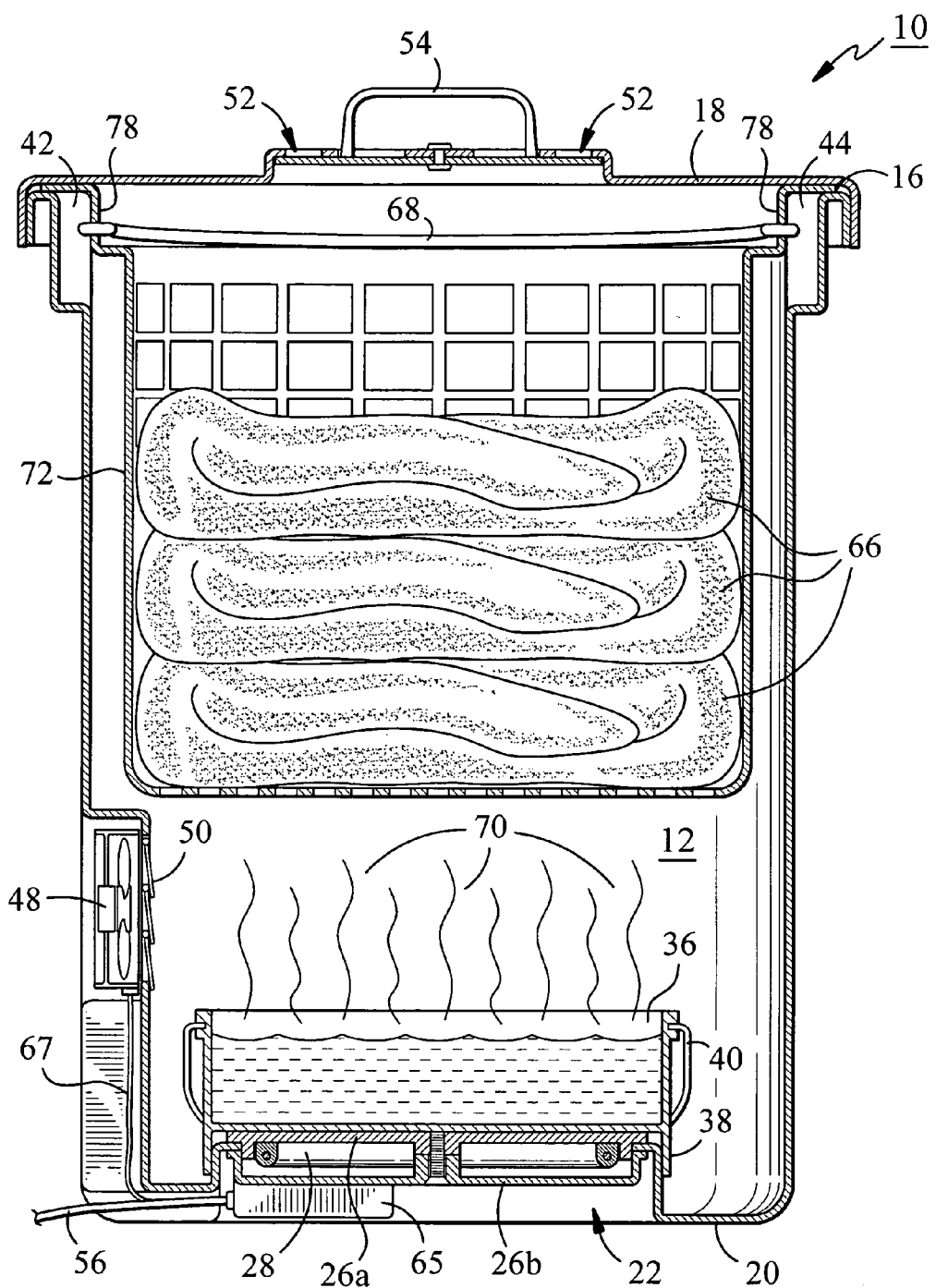
FIG. 4 is a view like FIG. 2, but with a bulk of fabric supported in a basket carried inside the sterilizer, this constituting another embodiment of the invention.
Figure 5:
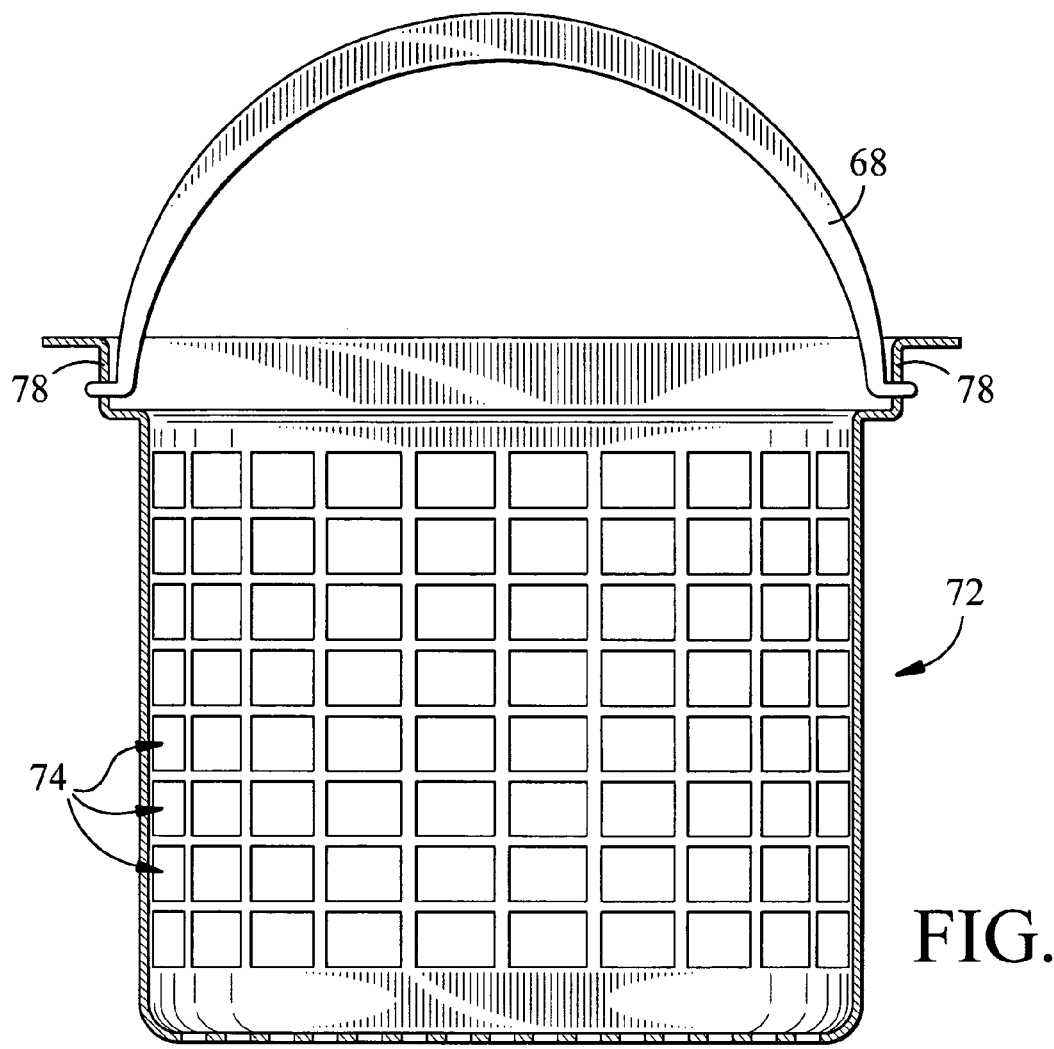
FIG. 5 is an axial section of the basket utilized in the sterilizer of FIG. 4.

Another aspect of the present invention is illustrated in FIG. 4, showing a modified arrangement for supporting the fabric to be treated. In place of the bar 46 of FIGS. 2 and 3, the invention provides for a wire-like basket 72, FIGS. 4 and 5, to be substituted therefor. The basket 72 is seen to have widely spaced, connecting spokes spaced from one another, to present a multiplicity of open spaces 74, and a curved, diametric wire handle 68 straddling the top of the basket. The handle 68 facilitates manipulation of the basket 72 when it is desired to insert it in the tub, or alternately remove it therefrom. The ends of the handle fit into eye-containing lugs 78, FIG. 5, that enable the handle to pivot, and assume a position to the side of the basket rim, by gravity. In contrast to the functioning of the first arrangement described in FIGS. 2 and 3, the basket 72 is adapted to hold a load of fabric 66 in a bulk form. In other respects the operation of the modified tub configuration utilizing the basket is similar to that already described in connection with the bar 46, and the heating cycles and vent arrangements therefrom are intended to be carried over to the present basket-style sterilizer.

The present invention may be embodied in other specific forms without departing from the spirit of any of the essential attributes thereof; therefore, the illustrated embodiments should be considered in all respects as illustrative and not restrictive, reference being made to the appended claims rather than solely to the foregoing description to indicate the scope of the invention.

Any appended claim represents an aspect of the invention which is separate and distinct from any other, and accordingly it is intended that any claim be treated as such when examined in the light of the prior art devices in any determination of novelty or validity.

Variations and modifications are possible without departing from the spirit of the invention.

LIST OF REFERENCE NUMERALS

10 Sterilizer device
12 Tub
14 Top of tub
16 Lip of tub
18 Lid for tub
20 Bottom wall of tub
22 Recess in bottom wall
26 Housing for heating element
26a Housing upper part
26b Housing lower part
28 Heating element
36 Metal pan, container
38 Pot flange
40 Pot handle
42 One of notch pair
44 Other of notch pair
46 Suspension rod, hanger, bar
48 Electric muffin fan
50 Gravity/air-operated shutters
52 Passive, manually operable shutter in lid
54 Handle of tub lid
56 Electric cord
58 Three prong plug
60 Timer and electrical switching module in cord
62 Switch for heating element
64 Switch for muffin fan
66 Clothing/fabric
67 Electric lead
68 Basket handle
70 Steam/water vapor
72 Basket
74 Spoke/hole configuration
78 Lug to receive handle
82 Arrows showing air/vapor flow The embodiments of the invention in which an exclusive property or privilege is claimed are defined as follows:

1. A household sterilizer apparatus for decontaminating soiled cloth material such as diapers or clothing, comprising in combination:
   a) an upright tub having an open top terminating in a lip, a bottom wall constituting a base, and a vertical side wall,
   b) a closure member adapted to fit over said tub lip,
   c) an electrical heater disposed at the base of the tub, said heater having a heat insulating outer housing, and an upper surface providing a hot plate,
   d) a removable metal pan having a diametric handle, said pan having a bottom wall adapted to be seated on said hot plate,
   e) a quantity of water in said pan, to be vaporized into steam and water vapor, said steam and water vapor filling the tub interior and coming into contact with the diapers or clothing so as to clean the same,
   f) a suspension structure consisting of a cross bar extending from one side of the tub interior to an opposite side thereof, for suspending said cloth material in the tub downward of the tub lip and in the path of the generated steam emanating from the metal pan, and
   g) an electrically powered venting fan disposed in the side wall of said tub, for introducing air from outside the tub into the tub interior, and displacing residual steam and water vapor therein, and
   h) an electrical control for either operating the venting fan or for interrupting power from the fan, accessible from outside of the tub.

2. The invention as set forth in claim 1, wherein:
   a) said electrical heater is powered through a control line having an electric switch in series with the line, said electric switch being a push-button type.

3. The invention as set forth in claim 1, wherein:
   a) said tub is constituted of molded substance, said cross bar being cradled between two diametrically opposed notches disposed in said lip of the tub, and said notches being integrally molded with the tub lip.

4. The invention as set forth in claim 1, wherein:
   a) said venting fan faces a gravity-operated shutter in the vertical side wall of the tub, arranged to open by air from the fan when it operates, and to close by gravity when the fan is dormant.

5. The invention as set forth in claim 4, and further including:

a) a passive vent in the closure member for the tub, said passive vent being manually operable from above the tub and being continuously adjustable from immediately above the closure member between open and closed positions, irrespective of the operation of the venting fan in the vertical side wall of the tub.

6. A household sterilizer apparatus for decontaminating soiled cloth material such as diapers or clothing, comprising in combination:
   a) an upright tub having an open top terminating in a lip, a bottom wall constituting a base, and having a vertical side wall,
   b) a closure member adapted to fit over said tub lip,
   c) an electrical heater disposed at the base of the tub, said heater having a heat insulating outer housing, and an upper surface providing a hot plate,
   d) a removable metal pan having a diametric handle, said pan having a bottom wall adapted to be seated on said hot plate,
   e) a quantity of water in said pan, to be vaporized into steam and water vapor,
   f) a suspension structure consisting of a porous basket for holding said cloth material, and a mounting in the tub for supporting the basket therein above the metal pan, said steam and water vapor filling the tub interior and coming into contact with the cloth material in the basket, so as to clean the same, and further including,
   g) an electric venting fan mounted in the vertical side wall of the tub, and
   h) a gravity-operated shutter, arranged to open via air from the fan when it operates, and to close by gravity when the fan is dormant.

7. The invention as set forth in claim 6, and further including:
   a) a passive vent in the closure member for the tub, said passive vent being manually operable from above the tub and being continuously adjustable from immediately above the closure member between open and closed positions, irrespective of the operation of the venting fan in the vertical side wall of the tub.

\* \* \* \* \*